(12) United States Patent
Heymann et al.

(10) Patent No.: US 10,271,922 B2
(45) Date of Patent: Apr. 30, 2019

(54) DEVICE FOR SHEILDING TEETH TO BE TREATED

(71) Applicant: Muhlbauer Technology GmbH, Hamburg (DE)

(72) Inventors: Rudolf Heymann, Hamburg (DE); Harald Pauls, Hamburg (DE); Sven Meyer, Apensen (DE)

(73) Assignee: Mühlbauer Technology GmbH, Hamburg (DE)

( * ) Notice: Subject to any disclaimer, the term of this patent is extended or adjusted under 35 U.S.C. 154(b) by 0 days.

(21) Appl. No.: 15/120,671

(22) PCT Filed: Feb. 24, 2015

(86) PCT No.: PCT/EP2015/053776
§ 371 (c)(1),
(2) Date: Aug. 22, 2016

(87) PCT Pub. No.: WO2015/124785
PCT Pub. Date: Aug. 27, 2015

(65) Prior Publication Data
US 2017/0367790 A1    Dec. 28, 2017

(30) Foreign Application Priority Data

Feb. 24, 2014 (DE) .................... 20 2014 001 569 U
Dec. 29, 2014 (DE) .................... 20 2014 010 138 U

(51) Int. Cl.
*A61C 5/82*    (2017.01)
*A61C 19/00*   (2006.01)
*A61C 5/00*    (2017.01)

(52) U.S. Cl.
CPC ................ *A61C 5/82* (2017.02); *A61C 19/00* (2013.01); *A61C 5/00* (2013.01)

(58) Field of Classification Search
CPC .... A61C 5/82; A61C 5/85; A61C 5/88; A61C 5/00; A61C 19/00
See application file for complete search history.

(56) References Cited

U.S. PATENT DOCUMENTS 2,092,549 A * 9/1937 Craigo .................... A61C 5/82
                                                       433/136
3,478,432 A   11/1969 Gross
(Continued)

FOREIGN PATENT DOCUMENTS

JP     S5631745        3/1981
WO     WO 9639984 A1 * 12/1996 ............... A61C 5/82

OTHER PUBLICATIONS

International Search Report and Written Opinion of PCT/EP2015/053776, dated May 4, 2015, 8 pages.

*Primary Examiner* — Heidi M Eide
(74) *Attorney, Agent, or Firm* — Casimir Jones, S.C.; Mary Ann D. Brow

(57) ABSTRACT

A device for shielding teeth to be treated in order to prevent an inflow of liquid, such as saliva or bloody the device comprising a partial dental dam (1) comprising a tensioning cloth (2) made of an elastic material designed to be introduced into at least one intermediate tooth space (11) when in an elongated state, and two actuation elements (3) arranged on opposing ends of the tensioning cloth (2) for use in pulling the tensioning cloth (2) into an elongated state, and use of the device for shielding teeth to be treated.

21 Claims, 6 Drawing Sheets

(56) References Cited

U.S. PATENT DOCUMENTS 5,499,917 A * 3/1996 Erickson .................. A61C 5/82
                                                               433/137
2004/0219486 A1   11/2004  Heasley

* cited by examiner

Fig. 2
a) 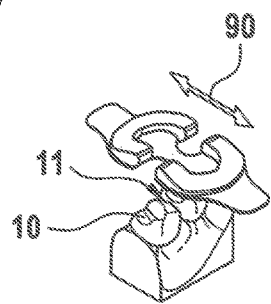
b) 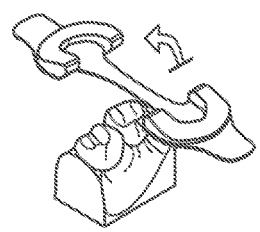
c) 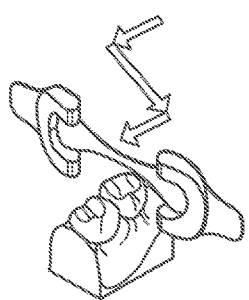
d) 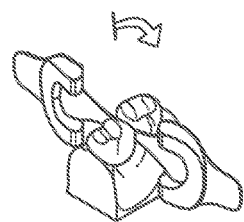
e) 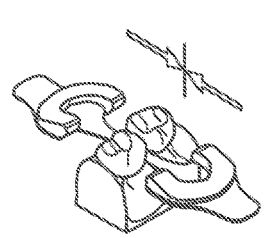
f) 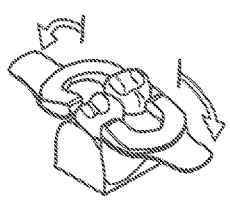
g) 

Fig. 3
a) 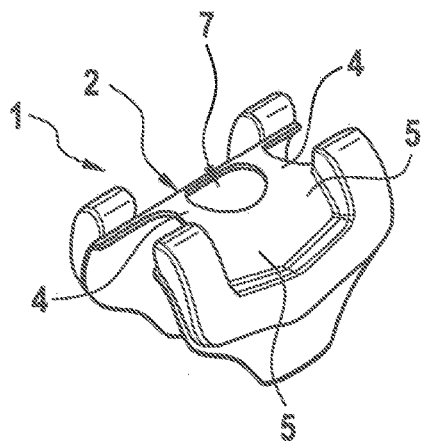
b) 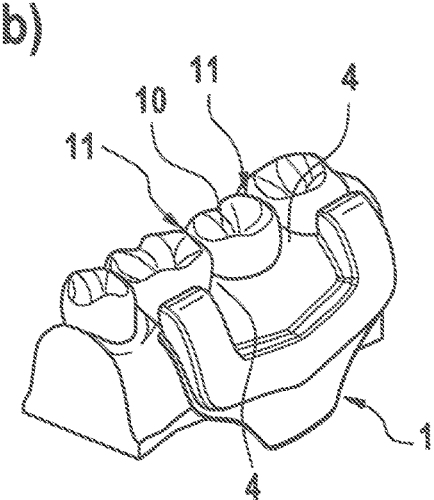

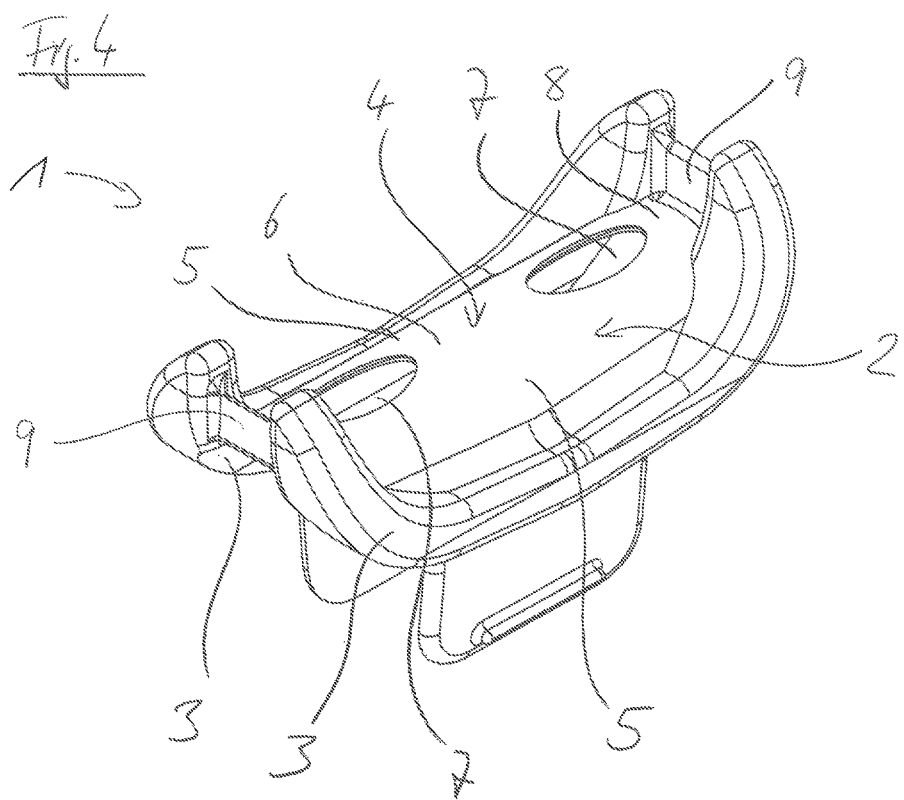

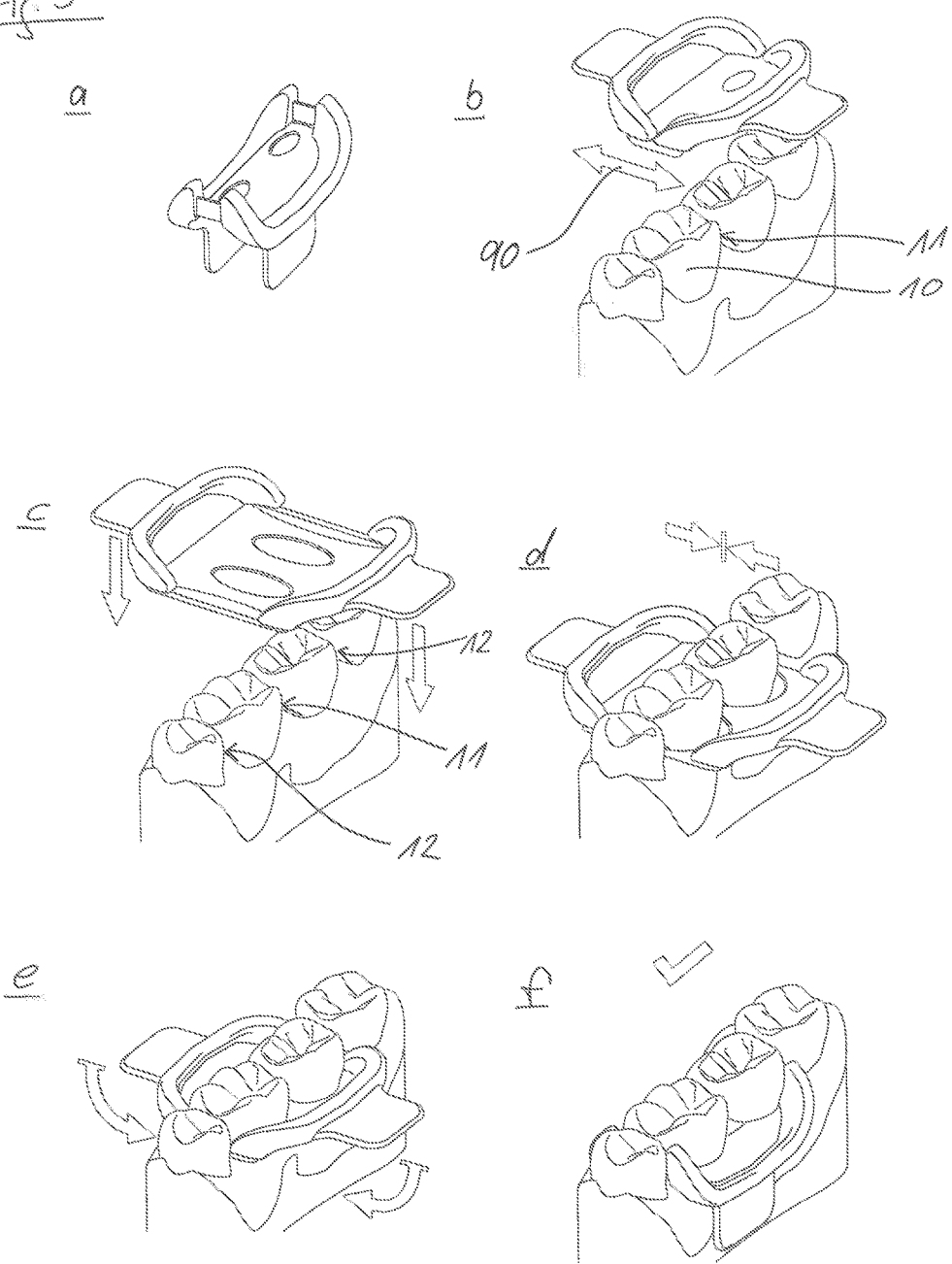

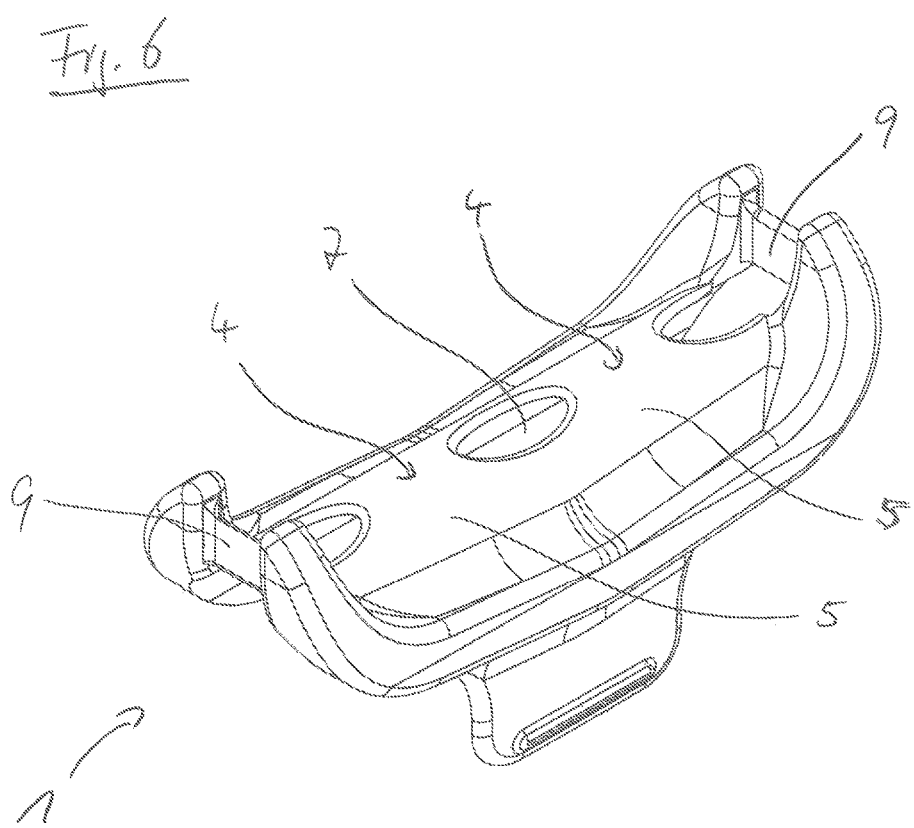

DEVICE FOR SHEILDING TEETH TO BE TREATED

The invention relates to a device for shielding teeth to be treated, in order to prevent the inflow of liquid, for example saliva or blood, and to a use of the device according to the invention.

It is known in the prior art, e.g. from WO 96/39984, to use a so-called dental dam to shield a tooth to be treated from the rest of the oral cavity, such that any inflow of saliva to the tooth to be treated is suppressed. At the same time, it is possible to prevent dental liquids, pastes or the like from coming into contact with teeth other than the one to be treated or from being swallowed. The dental dam can cover the entire oral cavity of a patient. However, dental dam cloths are also available which cover only a part of the oral cavity.

The dental dam is a liquid-impermeable cloth, in most cases made of elastic plastic or rubber, with an opening for the tooth to be treated. The dental dam has to be tensioned and clamped between the patient's teeth with clips, wedges and/or other aids. The application of a dental dam by a dentist is very time-consuming and is often unpleasant for the patient, or even painful. In view of the last-mentioned disadvantages, there is only a limited acceptance of dental dams in dental practice.

The object of the present invention is to make available a device for shielding teeth to be treated, which device no longer has the disadvantages known in the prior art or has these disadvantages only to a lesser extent.

This object is achieved by a partial dental dam according to the main claim and by the use according to the additional main claim. Advantageous developments are the subject matter of the dependent claims.

Accordingly, the invention relates to a partial dental dam for shielding teeth to be treated, comprising a tensioning cloth made of elastic material and two actuation elements arranged on opposite ends of the tensioning cloth, wherein the tensioning cloth is designed to be introduced into at least one interdental space from the occlusal side in a first tensioned state, which can be achieved by pulling the actuation elements apart in a tensioning direction, and to bear sealingly on the interdental gingiva and the approximal surfaces of the teeth forming the at least one interdental space in a second state after introduction into at least one interdental space, wherein the actuation elements, in the untensioned insertion state of the tensioning cloth, each bear on at least one tooth (preferably on the smooth surface of at least one tooth) and/or on the surrounding gingiva.

By means of the actuation elements being pulled apart, the tensioning cloth is elastically deformed in such a way that it can be easily introduced, depending on the design of the tensioning cloth, into one or more interdental spaces from the occlusal side. The elastic deformation results in a reduction in size of the cross section of the tensioning cloth, such that the latter can be easily introduced past the crowns into the interdental space. After the tensioning cloth has been introduced into the interdental space, the tension can be released, whereupon the tensioning cloth approximates to its original shape again. The tensioning cloth is thus placed tightly and sealingly on the teeth forming the at least one interdental space and on the interdental gingiva, and the desired shielding of the at least one interdental space is achieved.

In the second state, the actuation elements can bear on one or more teeth, in particular on the smooth surfaces thereof, and/or on the gingiva and thereby stabilize the partial dental dam. Additional fastening or clamping devices for securing the tensioning cloth are not necessary in the partial dental dam according to the invention and are not provided.

The invention is based on the recognition that many dental procedures do not require complete dry workingfield of the kind achieved by a dental dam according to the prior art. Instead, it is often enough to keep dry only the tooth to be treated or at least a partial field thereof. Such dry workingfield can be achieved with the partial dental dam according to the invention. The partial dental dam introduced into at least one interdental space can in fact prevent saliva or another liquid from flowing from the direction of the gingiva into the at least one interdental space.

Compared to a dental dam, the partial dental dam according to the invention affords the advantage that the dentist performing the treatment no longer has to handle a plurality of elements such as dental dam cloth and clamp elements. Moreover, in contrast to the prior art, instruments such as forceps or the like are not strictly needed for the use of the partial dental dam according to the invention. The partial dental dam according to the invention is easy to handle and can be applied quickly.

Preferably, the tensioning cloth has a number of webs corresponding to the number of intermediate spaces to be sealed off, which webs extend between the actuation elements. The webs can then each be introduced into an interdental space to be sealed off. If only one interdental space is to be sealed off, it is sufficient if the tensioning cloth has only one web. If more than one web is provided, a free space is provided between the webs, and individual teeth, in particular molars or premolars, can be guided through the free space.

The at least one web is preferably flat, wherein the thickness of the tensioning cloth in the area of a web (i.e. the extent perpendicular to the surface of the gingiva) in the second state is much less than the width of the respective web (i.e. the extent perpendicular to the tensioning axis and parallel to the surface of the gingiva). In the untensioned state of the partial dental dam, the thickness of the tensioning cloth or of a web is preferably less than or equal to 1 mm, more preferably between 0.1 mm and 0.5 mm, more preferably between 0.1 mm and 0.3 mm. A web, at its narrowest point, has a width of preferably 2 mm to 8 mm, more preferably of 3 mm to 7 mm, more preferably of 5 mm to 6 mm in the untensioned state. In an alternative embodiment, a web, at its narrowest point, can also preferably have a width of 1.5 mm to 5 mm, more preferably of 2 mm to 3 mm, more preferably of 2.5 mm in the untensioned state. The distance between the two actuation elements in the starting state, hence the length of the tensioning cloth in the untensioned state, is preferably less than 10 mm, more preferably 4 mm to 8 mm, more preferably 4.5 mm to 6.5 mm, more preferably 5.5 mm.

The at least one web is preferably configured in the shape of a rounded double T. In a corresponding web, the side areas of the web lying next to the actuation elements are therefore wider than a middle web that connects these areas, wherein the transitions from the middle web to the side areas are rounded. By virtue of the shape of a rounded double T, the correspondingly configured web easily bears sealingly on the two teeth between which the middle web of the double T is introduced.

If only one interdental space is to be sealed off, it is sufficient if only one web in the form of a rounded double T is provided. If more than one interdental space is to be sealed off, the tensioning cloth can have several double T webs arranged next to each other, wherein the number of the double T surfaces corresponds to the number of the interdental spaces to be sealed off, and the side areas of webs lying next to each other can transition into each other. For the treatment of the approximal surfaces of two adjacent teeth or the treatment of an individual tooth, a tensioning cloth with one web may thus be sufficient. For the treatment of the approximal surfaces of three adjacent teeth or for an MOD filling of an individual tooth, the tensioning cloth preferably has two double T webs.

To permit improved bearing of the actuation elements on at least one tooth and/or the gingiva in the second state of the partial dental dam according to the invention, at least one strap is preferably provided between the two actuation elements, wherein the strap extends in the plane of the at least one web and is designed in such a way that it can be introduced into an interdental space adjacent to an interdental space into which the at least one web is introduced. Like the at least one web, the at least one strap is elastically deformed in the first state of the partial dental dam according to the invention and, in the second state of the partial dental dam, supports the bearing of the actuation elements on at least one tooth and/or on the surrounding gingiva. The at least one strap can in this case be similar to the at least one web, although it does not have to bear sealingly on the interdental gingiva and the approximal surfaces of the teeth between which the strap is introduced.

It is preferable if two straps are provided, wherein the at least one web is arranged between the two straps.

The free space resulting between two adjacent webs or between a web and a strap is preferably round, circular or oval, preferably elliptic. In the case of an elliptic shape, the half-axis parallel to the middle webs of the two adjacent webs or parallel to the middle web of the web and to the longitudinal extent of the strap is preferably smaller than the half-axis lying perpendicular thereto. For example, the half-axes can be 1.1 mm and 2.5 mm long. In principle, the at least one free space is preferably dimensioned such that it is suitable for the passage of premolars or molars. By means of a corresponding design of the free space between two adjacent webs or between web and strap, the webs and/or straps can be easily introduced into interdental spaces in the first state of the partial dental dam according to the invention, wherein in each case one tooth is guided through said free space.

The actuation elements are preferably designed in one piece with the tensioning cloth. Moreover, the at least one strap can preferably be designed in one piece with the actuation element and with the tensioning cloth. Since in this case the actuation elements, like the tensioning cloth and/or the at least one strap, are made of basically elastic material, they are to be configured in terms of shape and size in such a way that they are substantially dimensionally stable even under tensile loading in the first state of the partial dental dam. The actuation elements can, preferably at least in parts, have a greater thickness than the tensioning cloth.

It is preferable if the partial dental dam, in the untensioned state, has an arc-shaped or U-shaped cross section, such that the tensioning cloth, in the untensioned state, has a curvature perpendicular to the middle web of the at least one web, and the two actuation elements are arranged in mirror symmetry about a plane normal to the direction of the middle web of the at least one web. Such a configuration of the partial dental dam makes it simpler to use.

It is preferable if the actuation elements are U-shaped, wherein the open end of the actuation elements preferably points toward the tensioning cloth. By a corresponding configuration, the supporting and stabilizing function of the actuation elements in the second state of the partial dental dam is improved.

In the case of an arc-shaped or U-shaped cross section of the partial dental dam in the untensioned state, the branches of the U-shaped actuation elements can protrude over the curved tensioning cloth. The respective opposite branches of the U-shaped actuation elements can then be connected to each other via elastically deformable auxiliary straps. In the untensioned state of the partial dental dam, the auxiliary straps then do not lie in a plane with the at least one web and/or one strap, and instead they extend at a distance therefrom. By means of corresponding auxiliary straps, the bearing of the actuation elements in the second state of the partial dental dam can be further improved, such that in particular the danger of the actuation elements slipping is further reduced. The auxiliary straps can be designed in one piece with the actuation elements.

Although no instruments are needed in principle for using the partial dental dam according to the invention, openings can nevertheless be provided in the actuation elements, and medical forceps, for example, can engage in said openings. With the aid of forceps, the partial dental dam can then be tensioned and introduced into interdental spaces that are only accessible with difficulty in cases of purely manual handling.

The tensioning cloth preferably has an elasticity of 1 to 4, more preferably of 2 to 3, with an almost complete restoring capacity. This means that a change of length of 100% to 400% or of 200% to 300% relative to the original length is possible with the tensioning cloth, without this causing visible plastic elongation. In other words, the tensile load, at the indicated elongation of the tensioning cloth, should lie below the elastic limit, at any rate at least below the 0.2% yield point of the tensioning cloth.

Preferably, the tensioning cloth has a tear strength of greater than 5 $N/mm^2$ as per DIN 53504:2009-10, wherein the tear strength can be determined in particular using S3 test bodies.

Suitable materials for the tensioning cloth and/or the actuation elements are all those materials that have sufficient elastic properties. Preferably, the tensioning cloth and/or the actuation elements are made of silicone or latex, more preferably of two-component silicones or a thermoplastic elastomer.

Liquid hot-crosslinking silicone rubbers or silicone elastomers, in particular addition-crosslinking silicone rubbers or silicone elastomers are particularly preferably used. An example of a corresponding material is ADDISIL™ 1140M silicone rubber (Momentive Performance Materials. Inc.), which has a tear strength of 12 $N/mm^2$ as per DIN 53504: 2009-10, a Shore A hardness of 42 as per DIN 53505 and an elongation at break of 940% as per DIN 53504.

The partial dental dam according to the invention is preferably produced as a multi-layer punched/bonded structure or as an injection-molded structure. In a multi-layer punch/bond method, several layers of punched-out material are bonded together, such that the final structural part has a layered configuration.

In the use of the partial dental dam according to the invention for shielding teeth to be treated, the tensioning cloth of the partial dental dam and, if appropriate, the straps and/or auxiliary straps are stretched by pulling the actuation elements apart in the tensioning direction, the tensioning cloth is introduced in the elongated state into at least one interdental space from the occlusal side, and the tensioning cloth is placed on the interdental gingiva and the approximal surfaces of the teeth forming the at least one interdental space by releasing the tensioning force of the tensioning cloth, wherein the actuation elements each bear on at least one tooth (preferably on the smooth surface of at least one tooth) and/or on the surrounding gingiva. For further explanation of the use, reference is made to the above statements concerning the partial dental dam according to the invention.

The invention is now described by way of example on the basis of illustrative embodiments and by reference to the attached drawings, in which:

FIG. 1 shows a first illustrative embodiment of a partial dental dam according to the invention;

FIGS. 2a-g show an example of a use of the partial dental dam from FIG. 1;

FIGS. 3a-3b show a second illustrative embodiment of a partial dental dam according to the invention;

FIG. 4 shows a third illustrative embodiment of a partial dental dam according to the invention;

Figure 1:
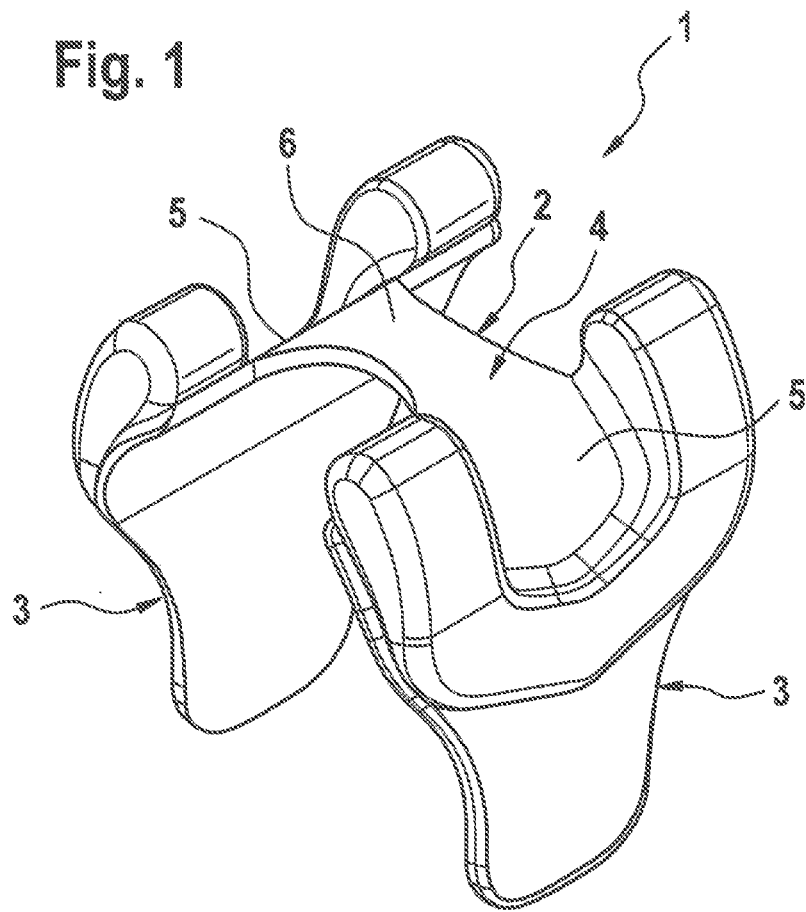

FIGS. 5a-f show an example of a use of the partial dental dam from FIG. 4; and

FIG. 6 shows a fourth illustrative embodiment of a partial dental dam according to the invention.

A first illustrative embodiment of a partial dental dam 1 according to the invention for shielding teeth to be treated is shown in FIG. 1. The partial dental dam 1 comprises a tensioning cloth 2 made of elastic material, and two actuation elements 3 which are integrally formed with the tensioning cloth 2 and are arranged on two opposite ends of the tensioning cloth 2.

The tensioning cloth 2 has a web 4 extending between the actuation elements 3, which web 4, as is explained below in connection with FIG. 2, is provided for introduction into an interdental space from the occlusal side. The web 4 is configured in the shape of a rounded double T, wherein the side areas 5 of the web 4 lying close to the actuation elements 3 are wider than the middle web 6 that connects these side areas 5. The transitions from the middle web 6 to the side areas 5 are rounded.

At its narrowest point, the web 4, in the untensioned state of the partial dental dam, has a width of 2.5 mm and a thickness of 0.5 mm. The length of the tensioning cloth in the state shown is 5.5 mm. The tensioning cloth has an elasticity of 3 with an almost complete restoring capacity, and a tear strength of greater than 5 N/mm$^2$, wherein the tear strength was determined according to DIN 53504:2009-10 using an S3 test body.

The actuation elements 3 are U-shaped, wherein the open end of the actuation elements 3 points toward the tensioning cloth 2. By corresponding shaping of the actuation elements 3, good stability of the partial dental dam 1 is achieved in the use explained below in connection with FIG. 2.

The actuation elements 3 are formed in one piece with the tensioning cloth 2 and, consequently, are made from the same elastic material as the tensioning cloth 2. However, in order to ensure sufficient stiffness of the actuation elements 3, these have a greater thickness than the tensioning cloth 2 in parts, in particular in the area of the U-shaped formation specifically.

The use of the partial dental dam 1 according to FIG. 1 is now explained with reference to FIG. 2. The partial dental dam 1 is introduced here into an interdental space 11 between two teeth 10.

Proceeding from the starting state shown in FIG. 2a, the partial dental dam 1 is tensioned by pulling the actuation elements 3 apart in a tensioning direction 90, wherein in particular the tensioning cloth 2 is elongated. The resulting first state of the partial dental dam 1 is shown in FIG. 2b.

As a result of the elongation of the tensioning cloth 2, the cross section of the web 4 decreases in size, such that the web 4 can already in principle be introduced into the interdental space 11 from the occlusal side. Since the partial dental dam 1 has only a single web 4, the introduction of the web 4 into the interdental space 11 can be further facilitated if the partial dental dam is tilted through 90° (cf. FIG. 2c). In this way, the web 4 does not have to be introduced into the interdental space 11 with the side defining the width first, but instead with the side defining the thickness. Since the thickness in the starting state is already smaller than the width and, in addition, is further reduced by the elongation of the tensioning cloth 2, the introduction of the web 2 into the interdental space is further facilitated.

The partial dental dam 1 accordingly tilted through 90° (cf. FIG. 2c) is introduced into the interdental space 11 (cf. FIG. 2d). Thereafter, the partial dental dam 1 is again tilted through 90° (cf. FIG. 2e) before the tensioning force of the tensioning cloth 2 is released, such that the actuation elements 3 bear on the teeth 10 (cf. FIG. 2f). By release of the tensioning force, the deformation of the tensioning cloth 2 reverses, and it again approximates to its original shape (cf. FIG. 2a). A tight bearing of the tensioning cloth 2 on the interdental gingiva and on the approximal faces of the teeth 10 is thus achieved. The desired shielding, for preventing the inflow of liquid, for example saliva or blood, is thus ensured.

Finally, the actuation elements 3 are pivoted in such a way that, in addition to bearing on the teeth 10, they additionally bear on the surrounding gingiva (cf. FIG. 2g). Good stabilization of the partial dental dam 1 and good accessibility to the treatment site are thus achieved.

As will be clear from FIG. 2 and from the associated explanations, no instruments are needed in principle to use the partial dental dam 1 according to the invention as shown in FIG. 1. Notwithstanding this, the actuation elements 3 can have openings (not shown) into which medical forceps can engage. With the aid of the forceps, the partial dental dam 1 can be tensioned and introduced into interdental spaces that are only accessible with difficulty in cases of purely manual handling.

FIG. 3 shows a second illustrative embodiment of a partial dental dam 1 according to the invention for shielding teeth to be treated, wherein FIG. 3b shows the partial dental dam 1 in the inserted state. The partial dental dam 1 shown in FIG. 3 corresponds in many aspects to that of FIG. 1, for which reason reference is made to the statements made there for explanatory purposes, and only the differences are discussed below.

In contrast to the tensioning cloth 2 of the partial dental dam from FIG. 1, the tensioning cloth 2 of the partial dental dam 1 from FIG. 3 has two webs 4, between which a free space 7 is provided through which an individual tooth can be guided. The webs 4 have a double T shape, wherein the side areas 5 of the two webs 4 merge into each other.

FIG. 3b shows the partial dental dam 1 in the inserted state, wherein the two webs 4 are introduced into a respective interdental space 11 and a tooth 10 is guided through the free space 7. The use of the partial dental dam from FIG. 3 is comparable to the use shown in FIG. 2, except that the partial dental dam 1 is not tilted for introduction into the interdental space 11, however (cf. FIGS. 2b and 2d).

In the illustrative embodiments according to FIGS. 1 and 3, the partial dental dam 1 in each case is produced by injection molding from two-component silicones, for example from ELASTOSIL® LR 3040/45 A/B as per data sheet version 1.3 (material number 60082563) or ELASTOSIL® LR 3040/50 A/B as per data sheet version 1.17

(material number 60071686) from Wacker Chemie AG. However, it is also possible to use another material, for example a thermoplastic elastomer, or another production method, for example a multi-layer punching/bonding method.

FIG. 4 shows a third illustrative embodiment of a partial dental dam 1 according to the invention, wherein the partial dental dam 1 is shown in its untensioned state. As will be seen directly from FIG. 4, the partial dental dam 1 has a U-shaped cross section in the untensioned state shown.

As in the preceding illustrative embodiments too, the partial dental dam 1 comprises an elastically deformable tensioning cloth 2, which extends between two actuation elements 3. The tensioning cloth 2 comprises a web 4 which is configured in the shape of a double T, and of which the side areas 5 lying close to the actuation elements 3 are wider than the middle web 6 lying between them. At its narrowest point, the web 4, in the untensioned state, has a width of 5.5 mm and a thickness of 0.3 mm.

Two straps 8 extend parallel to the web 4, on both sides of the latter, and the two actuation elements 3 are additionally connected to each other by these straps 8. At their narrowest point, the straps 8 have a width of 1.5 mm, and they are formed in one piece with the tensioning cloth 2. The free space 7 resulting in each case between web 4 and strap 8 has an elliptic shape, wherein the greater half-axis is 2.5 mm and the smaller half-axis is 1.1 mm. By way of this design, in the first state of the partial dental dam 1 in which the actuation elements 3 are pulled apart from each other, teeth can be more easily guided through the free spaces 7, and web 4 and strap 8 are introduced into the interdental space. This is explained in more detail below with reference to FIGS. 5a-f.

In the untensioned state shown, the tensioning cloth 2, in order to form the U-shaped cross section, extends in a curved shape in such a way that the two actuation elements 3 are arranged in mirror-symmetry about a central midplane. The actuation elements 3 are formed in one piece with the tensioning cloth 2 and are therefore made of the same elastic material as the tensioning cloth 2. In order to achieve increased stiffness in the area of the actuation elements 3, the latter have, in parts, a greater thickness than the tensioning cloth 2.

The actuation elements 3 are U-shaped, wherein the respectively open end of the actuation elements 3 points to the tensioning cloth 2. On account of the curvature of the tensioning cloth 2, the branches of the U-shaped actuation elements 3 protrude beyond the tensioning cloth 2. In this area protruding beyond the tensioning cloth 2, the opposite branches of the actuation elements 3 are connected to each other by auxiliary straps 9, which are formed in one piece with the actuation elements 3 and are thus made of the same elastic material as the actuation elements 3 and the tensioning cloth 2. These elastically deformable auxiliary straps 9 further improve the fit of the partial dental dam 1 in the state of use. The auxiliary straps 9 are ca. 2 mm wide in the direction perpendicular to the tensioning cloth 2 and have a thickness of ca. 0.3 mm.

The partial dental dam 1 shown in FIG. 4 is produced in one piece by injection molding. The material of the partial dental dam 1 is ADDISIL™ 1140M silicone rubber (Momentive Performance Materials, Inc.), which has a tear strength of 12 N/mm$^2$ as per DIN 53504:2009-10, a Shore A hardness of 42 as per DIN 53505 and an elongation at break of 940% as per DIN 53504.

FIGS. 5a-f show the use of the partial dental dam 1 from FIG. 4. The web 4 of the partial dental dam 1 is in this case intended to be introduced into an interdental space 11 between two teeth 10, in order to shield this interdental space 11 from the rest of the oral cavity.

Proceeding from the starting state shown in FIG. 5a, the partial dental dam 1 is tensioned by pulling the actuation elements 3 apart in a tensioning direction 90 (cf. FIG. 5b), wherein in particular the tensioning cloth 2 with the web 4 and the straps 8 is elongated. The auxiliary straps 9 are also elongated. The resulting first state of the partial dental dam 1 is shown in FIG. 5c.

In the elongated first state, the web 4 can be easily introduced into the interdental space 11 on account of the associated deformation. The straps 8 and auxiliary straps 9 are at the same time introduced into the interdental spaces 12 adjacent to the interdental space 11 into which the web 4 is introduced. In other words, the teeth 10 forming the interdental space 11 are guided through the free spaces 7 in the tensioning cloth 2 of the partial dental dam 1.

Once web 6 and straps 8, 9 have been introduced into the corresponding interdental spaces 11, 12, the partial dental dam 2 is untensioned again (cf. FIG. 5d). By release of the tensioning force, the deformation of the tensioning cloth 2 reverses, and the web 4 bears sealingly on the interdental gingiva and on the approximal surfaces of the teeth 10. The desired shielding, for preventing the inflow of liquid, for example saliva or blood, is thus ensured.

Finally, the actuation elements 3 are pivoted in such a way (cf. FIG. 5e) that they bear on the teeth 10 and also on the surrounding gingiva (cf. FIG. 5f). Good stabilization of the partial dental dam 1 and good accessibility to the treatment site are thus achieved.

As will be clear from FIG. 5 and from the associated explanations, no instruments are again needed in principle to use the partial dental dam 1 according to the invention as shown in FIG. 4. Notwithstanding this, the actuation elements 3 can have openings (not shown) into which medical forceps can engage. With the aid of the forceps, the partial dental dam 1 can be tensioned and introduced into interdental spaces that are only accessible with difficulty in cases of purely manual handling.

FIG. 6 shows a further illustrative embodiment of a partial dental dam 1 according to the invention for shielding teeth to be treated. The partial dental dam 1 shown in FIG. 6 corresponds in many aspects to that of FIG. 4, for which reason reference is made to the statements made there for explanatory purposes, and only the differences are discussed below.

In contrast to the tensioning cloth 2 of the partial dental dam from FIG. 4, the tensioning cloth 2 of the partial dental dam 1 from FIG. 6 has two webs 4, between which a free space 7 is provided through which an individual tooth can be guided. The webs 4 have a double T shape, wherein the side areas 5 of the two webs 4 merge into each other. The free space 7 has an elliptic shape.

In contrast to the illustrative embodiment from FIG. 4, the partial dental dam 1 in FIG. 6 is provided only with auxiliary straps 9, not with straps 8.

However, straps 8 may of course also be provided in the partial dental dam 1 according to FIG. 6.

When using the partial dental dam 1 from FIG. 6, the webs 4 are introduced into two adjacent interdental spaces 11, while the auxiliary straps 9 are introduced into the interdental spaces 12 adjoining on both sides. The partial dental dam 1 is here produced by injection molding from the same material as that of FIG. 4.

The invention claimed is:

1. A partial dental dam (1) for shielding teeth to be treated, comprising a tensioning cloth (2) made of elastic material and two actuation elements (3) arranged on opposite ends of the tensioning cloth (2), wherein a length of the tensioning cloth (2) in an untensioned state of the partial dental dam (1) is a distance between the two actuation elements (3);

wherein the tensioning cloth (2) comprises at least one web (4) as a portion of the tensioning cloth (2) to be introduced into at least one interdental space (11) from an occlusal side of teeth (10) that form the at least one interdental space (11), wherein the at least one web (4) is introduced into the at least one interdental space (11) in a first tensioned state of partial dental dam (1) that is achieved by pulling the actuation elements (3) apart in a tensioning direction (90), and wherein, after introduction into the at least one interdental space (11) and in a second tensioned state of the partial dental dam (1), the at least one web (4) will bear sealingly on interdental gingiva and the approximal surfaces of the teeth (10) that form the at least one interdental space (11), wherein the actuation elements (3) each bear on at least one tooth (10) and/or on surrounding gingiva in the second tensioned state, wherein in the untensioned state of the partial dental dam (1) the tensioning cloth (2) is curved across a width of the at least one web (4) around an axis perpendicular to tensioning direction (90), and wherein the actuation elements (3) are U-shaped to provide each actuation element (3) with an open end between two branches, wherein the open ends of the U-shapes of the two actuation elements (3) point toward the tensioning cloth (2), wherein each branch of one U-shaped actuation element (3) opposes a branch of the U-shaped actuation element (3) on the opposite end of the tensioning cloth (2), and wherein opposing branches of the U-shaped actuation elements (3) are connected to each other via elastically deformable auxiliary straps (9).

2. The partial dental dam as claimed in claim 1, wherein the tensioning cloth (2) has an elasticity of 1 to 4, with an almost complete restoring capacity.

3. The partial dental dam as claimed in claim 2, wherein the tensioning cloth (2) has an elasticity of 2 to 3.

4. The partial dental dam as claimed in claim 1, wherein the tensioning cloth (2) has a tear strength of greater than 5 N/mm$^2$ as per DIN 53504:2009-10.

5. The partial dental dam as claimed in claim 1, wherein the at least one web comprises a plurality of webs (4) that correspond in number to a plurality of intermediate interdental spaces (11) to be sealed off, wherein each web (4) of the plurality of webs is introduced from the occlusal side into one of said plurality of interdental spaces (11).

6. The partial dental dam as claimed in claim 1, wherein the at least one web (4) comprises side areas (5) close to the actuation elements (3) and a middle web (6) connecting the side areas (5), wherein the widths of said side areas (5) and said middle web (6) are perpendicular to the length of the tensioning cloth, and wherein the width of middle web (6) is less than widths of the side areas (5).

7. The partial dental dam as claimed in claim 6, wherein a narrowest width of middle web (6) of the at least one web (4) is 2 mm to 8 mm in the untensioned state of the partial dental dam (1), and/or wherein the length of the tensioning cloth (2) is less than 10 mm in the untensioned state of the partial dental dam (1).

8. The partial dental dam as claimed in claim 7, wherein the narrowest width of middle web (6) is 3 mm to 7 mm in the untensioned state of the partial dental dam (1).

9. The partial dental dam as claimed in claim 7, wherein the narrowest width of middle web (6) is 5 mm to 6 mm in the untensioned state of the partial dental dam (1).

10. The partial dental dam as claimed in claim 7, wherein the length of the tensioning cloth (2) is 4 mm to 8 mm in the untensioned state of the partial dental dam (1).

11. The partial dental dam as claimed in claim 7, wherein the length of the tensioning cloth (2) is 4.5 mm to 6.5 mm in the untensioned state of the partial dental dam (1).

12. The partial dental dam as claimed in claim 7, wherein the length of the tensioning cloth (2) is 5.5 mm in the untensioned state of the partial dental dam (1).

13. The partial dental dam as claimed in claim 6, wherein the two actuation elements (3) are arranged in mirror symmetry about a plane normal to the direction of the middle web (6) of the at least one web (4).

14. The partial dental dam as claimed in claim 1, wherein the at least one web (4), in the untensioned state of the partial dental dam (1), has a thickness of less than or equal to 1 mm.

15. The partial dental dam as claimed in claim 14, wherein the at least one web (4), in the untensioned state of the partial dental dam, has a thickness of between 0.1 mm and 0.5 mm.

16. The partial dental dam as claimed in claim 14, wherein the thickness of the at least one web (4) of the tensioning cloth in the untensioned state is between 0.1 mm and 0.3 mm.

17. The partial dental dam as claimed in claim 1, wherein at least one strap (8) is provided between and connected to the two actuation elements (3), wherein the at least one strap (8) extends in a plane of the at least one web (4), wherein the at least one strap (8) is designed to be introduced into an interdental space (12) adjacent to an interdental space (11) into which the at least one web (4) is introduced.

18. The partial dental dam as claimed in claim 17, wherein the at least one strap (8) comprises two straps (8), wherein the at least one web (4) is arranged between the two straps (8).

19. The partial dental dam as claimed in claim 1, wherein a free space (7) formed between the at least one web (4) and an adjacent web or between the at least one web (4) and a strap (8) is round, circular, oval, or elliptic.

20. The partial dental dam as claimed in claim 1, wherein the actuation elements (3) are designed in one piece with the tensioning cloth (2), with at least one strap (8) and/or the at least one auxiliary strap (9), wherein the actuation elements (3) have a greater thickness than the tensioning cloth (2).

21. A method of using a partial dental dam as claimed in claim 1, wherein i) elongating the tensioning cloth (2) by pulling on the actuation elements (3) in the tensioning direction (90) with a tensioning force, ii) introducing the at least one web (4) of the elongated tensioning cloth (2) into at least one interdental space (11), and iii) placing the tensioning cloth (2) on interdental gingival and approximal surfaces of the teeth (10) forming the at least one interdental space (11) by releasing the tensioning force, wherein the actuation element (3) each bear sealingly on at least one tooth (10) and/or on surrounding gingiva.

\* \* \* \* \*